United States Patent [19]

Yoshikumi et al.

[11] 4,451,457

[45] May 29, 1984

[54] CYCLODEXTRIN AND METHOD FOR PROMOTING THE PROLIFERATION OF INTESTINAL BIFIDOBACTERIA

[75] Inventors: Chikao Yoshikumi, Kunitachi; Katsuo Sakurai, Hino; Yoshio Omura, Funabashi; Mayumi Nohara, Ryugasaki; Takao Ando, Nerima; Isamu Motokawa, Hino, all of Japan

[73] Assignee: Kureha Kagaku Kogyo Kabushiki Kaisha, Nihonbashi, Japan

[21] Appl. No.: 347,726

[22] Filed: Feb. 10, 1982

[30] Foreign Application Priority Data

Feb. 18, 1981 [JP] Japan ................................. 56-22620

[51] Int. Cl.³ .......................................... A61K 31/715
[52] U.S. Cl. ................................................... 424/180
[58] Field of Search ......................................... 424/180

[56] References Cited

U.S. PATENT DOCUMENTS

| 4,352,793 | 10/1982 | Yamahira et al. | 424/180 |
| 4,352,794 | 10/1982 | Koch | 424/180 |

FOREIGN PATENT DOCUMENTS

| 18773 | 11/1980 | European Pat. Off. |
| 1450960 | 9/1976 | United Kingdom . |
| 2037306 | 7/1980 | United Kingdom . |
| 1573965 | 8/1980 | United Kingdom . |
| 2045081 | 10/1980 | United Kingdom . |

OTHER PUBLICATIONS

Chemical Abstracts, vol. 97 (1982), p. 385, C.A. #168905a.

*Primary Examiner*—Johnnie R. Brown
*Assistant Examiner*—Elli Peselev
*Attorney, Agent, or Firm*—Wegner & Bretschneider

[57] ABSTRACT

Disclosed is an agent comprising cyclodextrin as the active ingredient and a method for using such agent to promote the proliferation of intestinal bifidobacteria in animals.

5 Claims, No Drawings

CYCLODEXTRIN AND METHOD FOR PROMOTING THE PROLIFERATION OF INTESTINAL BIFIDOBACTERIA

This invention relates to an agent for promoting the proliferation of bifidobacteria.

The term "bifidobacteria" is used herein as a general term for the bacteria belonging to the genus Bifidobacterium (refer to Bergey's Manual of Determinative Bacteriology; (Eighth Edition), pp 659–676, Baltimore, The Williams & Wilkins Company) which have been known as the useful bacteria inhabiting in the human intestines. Namely, bifidobacteria play important roles in maintaining human health of preventing intestinal infection and supplying nutrients to the host without producing any noxious substances such as amines and ammonia.

Particularly it is said that the morbidity and mortality are higher in the bottle-fed babies than in the breast-fed babies since the number of bifidobacteria in the intestines of the former is smaller than that of the latter, and the need of the intestinal proliferation of bifidobacteria has increased greatly.

On the other hand, in consideration of the usefulness of bifidobacteria as mentioned above, it has been proposed to administer bifidobacteria themselves as a pharmaceutical and various kinds of preparations containing bifidobacteria have come to be commercially available.

However, bifidobacteria are generally unstable and liable to die during storage for a long period, and accordingly, it is considered difficult to maintain a desired amount of viable bifidobacteria in the preparation. Further, it is difficult for bifidobacteria to fix or proliferate for long period in the intestines although viable bifidobacteria are administered artificially.

The inventors have studied the intestinal proliferation of bifidobacteria, found that the proliferation of only bifidobacteria is remarkably promoted without affecting other intestinal bacteria when cyclodextrin is administered to a man, and then achieved this invention.

Namely, in the invention, bifidobacteria are not introduced from outside into the living body but are proliferated in the living body.

The bifidobacteria-proliferating agent of the invention contains cyclodextrin as an active ingredient. Cyclodextrin used in the invention includes $\alpha$-, $\beta$- and $\gamma$-cyclodextrin. The physicochemical properties of these cyclodextrins are shown in Table 1.

TABLE 1

| | α-cyclodextrin | β-cyclodextrin | γ-cyclodextrin |
|---|---|---|---|
| Number of glucose unit | 6 | 7 | 8 |
| Molecular weight | 973 | 1135 | 1297 |
| Diameter of cavity (Å) | 5–6 | 7–8 | 9–10 |
| Depth of cavity (Å) | 7–8 | 7–8 | 7–8 |
| Crystal form [1] | acicular | prismatic | prismatic |
| Specific rotatory power [2] | +150.5° | +162.5° | +177.4° |
| Solubility in water (g/100 ml at 25° C.) | 14.5 | 1.85 | 23.2 |

Notes:
[1] recrystallized from water
[2] $[\alpha]_D^{25}$ (in water)

Toxicity and pharmacological activities of cyclodextrins used in the invention were examined as follows.

(1) Acute toxicity

Each cyclodextrin ($\alpha$-, $\beta$- and $\gamma$-) was administered via the following routes to rats and mice and $LD_{50}$ was measured. The results are shown in Table 2.

TABLE 2

| Route of administration | Laboratory animal | | $LD_{50}$ (g/kg) | | |
|---|---|---|---|---|---|
| | | | α-cyclodextrin | β-cyclodextrin | γ-cyclodextrin |
| Oral | Mouse | ♂ | >12.5 | >12.5 | >12.5 |
| | | ♀ | >12.5 | >12.5 | >12.5 |
| | rat | ♂ | >12 | >12 | >12 |
| | | ♀ | >12 | >12 | >12 |
| Subcutaneous | Mouse | ♂ | >0.9 | >0.9 | >0.9 |
| | | ♀ | >0.9 | >0.9 | >0.9 |
| | rat | ♂ | >1.5 | >1.5 | >1.5 |
| | | ♀ | >1.5 | >1.5 | >1.5 |
| Intraperitoneal | Mouse | ♂ | >0.9 | >0.9 | >0.9 |
| | | ♀ | >0.9 | >0.9 | >0.9 |
| | rat | ♂ | >1.2 | >1.2 | >1.2 |
| | | ♀ | >1.2 | >1.2 | >1.2 |

As seen from Table 2, cyclodextrins used in the invention have low acute toxicity.

(2) Antibacterial activity

The antibacterial activity of cyclodextrin against the following bacteria was examined by the agar plate dilution method according to the Standard Method published by the Japanese Society of Chemotherapy. The test methods are as follows:

(a) Antibacterial activity against aerobic bacteria

| Species of bacteria tested | Deposition No. of the strain |
|---|---|
| Escherichia coli | IFO 12734 |
| Staphylococcus aureus | IAM 1011 |
| Bacillus subtilis | IAM 1069 |

After inoculating each bacteria in the Trypto-soya bouillon culture medium and incubating for 18 hours at 37° C., an aqueous suspension containing $10^8$ cells of the proliferated bacteria per ml was prepared. An agar plate was prepared by mixing one part by volume of each aqueous solution containing $\alpha$-, $\beta$- or $\gamma$-cyclodextrin at the concentrations of 400, 800 or 1600 μg per ml with nine parts by volume of Heart Infusion Agar culture medium as a culture medium for examining the drug sensitivity and pouring the mixed culture medium into each Petri dish.

After smearing each aqueous suspension of the bacteria onto the surface of the agar plate by drawing a line of 2 cm in length with a platinum loop, the bacteria was incubated for 18 hours at 37° C. and the concentration of cyclodextrin in the culture medium at which the growth of the bacteria was completely inhibited was adopted as MIC (minimum inhibiting concentration).

(b) Antibacterial activity against anaerobic bacteria

| Species of bacteria tested | Deposition No. of the strain |
|---|---|
| Bacteroides fragilis | ATCC 25285 |
| Lactobacillus casei | IAM 1118 |
| Bifidobacterium bifidum | ATCC 15696 |
| Bifidobacterium adolescentis | ATCC 15703 |
| Bifidobacterium infantis | ATCC 15697 |
| Bifidobacterium pseudolongum | ATCC 25526 |

Except for using GAM bouillon culture medium as the medium for proliferating the bacteria and GAM agar culture medium for examining the drug sensitivity of the bacteria, and for incubating the inoculated culture medium by Gaspak method (concentration of carbon dioxide of 5% by volume) for 24 hours at 37° C., the MIC was obtained in the same procedures as in (a).

The results of tests in (a) and (b) showed the MIC of every type of cyclodextrin was larger than 1600 μg/ml of aqueous suspension, the fact showing cyclodextrin has no appreciable antibacterial activity.

(3) Mutagenicity

Mutagenicity of cyclodextrin was examined according to the method described in "Guidebook for Test of Mutagenicity by Microorganisms" (edited by Section of Research for Chemical Substances, Department of Safety and Health, Ministry of Labour, Japan).

After incubating for 20 min at 37° C. the mixture of 0.5 ml of phosphate buffer, 0.05 ml of the aqueous cyclodextrin solution (α-, β- or γ-cyclodextrin being of 5000 μg per plate even at the highest concentration) and 0.1 ml of aqueous suspension of Salmonella typhimurium TA 98 or TA 100 both of which have been originally isolated by Ames et al. and obtained from National Institute of Genetics, Japan as the test bacterium, the incubated bacterial culture was layered on the minimum culture medium, and the layered culture was incubated for 48 hours at 37° C. The number of the revertant colonies in the culture medium was then counted.

The number of revertant colonies of each bacterial strain showed no significant increase as compared to that of control (water was added instead of aqueous solution of cyclodextrin).

As seen from the results of (3), cyclodextrin showed substantially no mutagenicity.

The activity of cyclodextrin in promoting the intestinal proliferation of bifidobacteria was recognized by the results of test as described below. Namely, cyclodextrin was administered orally to test animals such as mouse at the dose of 2 g/kg of body weight per day for 2 weeks, and the number of viable intestinal bacteria such as bifidobacteria, Escherichia coli, Lactobacilli and Bacteroides sp. in the feces of the test animal seven days after the administration were counted by the conventional method. Cyclodextrin showed a remarkable effect in specifically promoting the intestinal proliferation of only bifidobacteria at a rate as high as 90 times. Namely, when the bifidobacteria-proliferating agent of the invention is administered to the living body, it is possible to proliferate only bifidobacteria in the intestine of the living body without disturbing the intraintestinal bacterial flora.

Accordingly, the bifidobacteria-proliferating agent of the invention brings about the improving effect on the symptoms of intestinal diseases such as diarrhea, enteritis, indigestion and constipation, and also is useful as a therapeutic drug for hepatogenous encephalopathy.

Furthermore, by adding cyclodextrin of the invention into food stuffs, drinks and table luxuries, it is also possible to aim the proliferation of intestinal bifidobacteria.

In order to apply cyclodextrin as a bifidobacteria-proliferating agent, it is preferable to use cyclodextrin singly or as a mixture with pharmaceutically acceptable diluent or other drug while supplying in a dosage unit form according to pharmaceutical composition. For example, the pharmaceutical composition can take various forms such as powder, granule, tablet, sugar-coated tablet, capsule, suspension. solution, emulsion and ampoule.

In addition, as a diluent, solid substances, liquid substances, semisolid substances may be used, or orally ingestable capsule may be included in the diluent. As a concrete diluent, for example, vehicles, extenders, conjugating agents, wetting agents, disintegrants, surfactants, slipping agents, dispersing agents, buffers, perfumes, preservatives, assisting agents to dissolve and solvents may be enumerated. Diluent is singly used or in combination of more than two kinds.

The proliferating agent of the invention contains 0.01 to 100% by weight of cyclodextrin as an active ingredient in usual cases, and is administered orally or parenterally, however, oral administration is preferable.

The dosage of the agent for promoting the intestinal proliferation of bifodobacteria of the invention depends on the species, the age, the symptom and the individual difference of the host, however, in the ordinary cases where oral administration is carried out to a man, 0.01 to 1 g may be administered per kg of body weight per day, preferably 0.1 to 0.5 g/kg/day, the actual administration being carried out 1 to 4 times/day with the divided daily dose by one to four.

The advantages of the invention will be illustrated while referring to the following examples:

EXAMPLE 1

Two kinds of aqueous solution each containing 20% by weight of α-cyclodextrin or γ-cyclodextrin, and one kind of aqueous suspension containing 20% by weight of β-cyclodextrin were prepared as well as one kind of aqueous solution containing 20% by weight of dextrin as control.

Each solution or suspension was administered to female C3H/He mice at 8th week after birth, one group consisting of 5 animals and the number of groups being four, the dosage being 2.0 g of cyclodextrin/kg of body weight/day, continuously for 2 weeks.

Before and 7 days after the administration, feces of each mouse was collected, and after diluting the collected feces with 100 times by weight of an anaerobic phosphate buffer and grinding the diluted feces, each 0.1 ml of the ground feces was inoculated on each culture medium (refer to Table 3) for the specified bacterial species, and the thus inoculated culture media were incubated at 37° C. for one to five days under the aerobic conditions or anaerobic conditions (according to the anaerobic grove box method).

TABLE 3

| Bacterial species | Culture medium | Culture Conditions |
|---|---|---|
| bifidobacteria | BS agar | anaerobic, 37° C., 5 days |
| Lactobacilli | LBS agar | same as above |
| Bacteroides sp. | NBGT agar | same as above |
| Escherichia coli | DHL agar | aerobic, 37° C., one day |

After the incubation was over, the number of bifidobacteria, *Escherichia coli*, Lactobacilli and Bacteroides sp. in the culture medium was counted. The results are shown in Tables 4 to 7, the counts being the average of five mice.

TABLE 4

α-cyclodextrin

| Bacterial species | Viable count[1] before (A) administration | 7 days after (B) administration | Rate of proliferation (B/A) |
|---|---|---|---|
| bifidobacteria | $5.4 \times 10^5$ | $6.5 \times 10^7$ | 120 |
| Lactobacilli | $8.8 \times 10^8$ | $8.8 \times 10^8$ | 1.00 |
| Bacteroides sp. | $8.6 \times 10^8$ | $8.4 \times 10^8$ | 0.98 |
| *Escherichia coli* | $6.2 \times 10^6$ | $9.0 \times 10^6$ | 1.45 |

Note:
[1] per g of the feces.

TABLE 5

β-cyclodextrin

| Bacterial species | Viable count[1] before (A) administration | 7 days after (B) administration | Rate of proliferation (B/A) |
|---|---|---|---|
| bifidobacteria | $1.3 \times 10^5$ | $1.8 \times 10^8$ | 1385 |
| Lactobacilli | $1.5 \times 10^9$ | $2.2 \times 10^9$ | 1.47 |
| Bacteroides sp. | $3.5 \times 10^8$ | $3.7 \times 10^8$ | 1.06 |
| *Escherichia coli* | $4.0 \times 10^6$ | $5.8 \times 10^6$ | 1.45 |

Note:
[1] per g of the feces.

TABLE 6

γ-cyclodextrin

| Bacterial species | Viable count[1] before (A) administration | 7 days after (B) administration | Rate of proliferation (B/A) |
|---|---|---|---|
| bifidobacteria | $2.0 \times 10^4$ | $1.8 \times 10^6$ | 90 |
| Lactobacilli | $9.0 \times 10^8$ | $7.0 \times 10^8$ | 0.78 |
| Bacteroides sp. | $1.0 \times 10^8$ | $3.0 \times 10^8$ | 3.00 |
| *Escherichia coli* | $7.5 \times 10^6$ | $7.0 \times 10^6$ | 0.93 |

Note:
[1] per g of the feces.

TABLE 7 dextrin (for comparison)

| Bacterial species | Viable count[1] before (A) administration | 7 days after (B) administration | Rate of proliferation (B/A) |
|---|---|---|---|
| bifidobacteria | $2.3 \times 10^5$ | $1.6 \times 10^5$ | 0.70 |
| Lactobacilli | $5.0 \times 10^8$ | $6.0 \times 10^8$ | 1.20 |
| Bacteroides sp. | $3.2 \times 10^8$ | $8.0 \times 10^8$ | 2.50 |
| *Escherichia coli* | $9.0 \times 10^6$ | $7.2 \times 10^6$ | 0.80 |

Note:
[1] per g of the feces.

As seen in Tables 4 to 6, cyclodextrin specifically proliferated only bifidobacteria in the intestines of the living body at a proliferation rate of higher than 90 times, and on the other hand, dextrin did not exhibit such an activity to the proliferation of bifidobacteria as seen from Table 7. In addition, no abnormality was observed on the feces of all animals administered with cyclodextrin.

EXAMPLE 2

Ten parts by weight of α-, β- or γ-cyclodextrin, 15 parts by weight of heavy magnesium oxide and 75 parts by weight of lactose were uniformly mixed to prepare powdery compositions. In addition, by putting the powdery compositions into capsules, capsuled compositions were prepared.

EXAMPLE 3

This example shows an application of the capsuled composition containing β-cyclodextrin as an active ingredient to normal persons.

To three healthy male adult volunteers, the capsulated composition prepared in Example 2 was administered daily for 2 weeks continuously at a dosage of 10 g of cyclodextrin/day. Before and after the total administration, feces specimens were collected from the three persons, and according to the procedures shown in Example 1, the numbers of bacteria (including bifidobacteria) in the specimen were determined.

As a result of determinations, it was observed that the number of bifidobacteria in the feces collected after administration showed an increase of about 10 to 100 times as compared to that in the feces collected before administration. In addition, in the feces of the person whose feces contained a relatively large number of bifidobacteria before administration, such a remarkable increase of the number of bifidobacteria was not observed in the feces collected after administration from the person.

What is claimed is:

1. A method for promoting the proliferation of bacteria of the genus Bifidobacterium in the intestines of animals which comprises administering cyclodextrin to animals at the rate of 0.01 to 1 g per kg of body weight per day.

2. The method according to claim 1 wherein the rate of administration is 0.1 to 0.5 g per kg per day.

3. A method according to claim 1 wherein the cyclodextrin is beta cyclodextrin.

4. The method according to claim 1 wherein the cyclodextrin is administered in divided doses.

5. A method for promoting the proliferation of bacteria of the genus Bifidobacterium in the intestines of humans which comprises administering cyclodextrin to humans at the rate of 0.01 to 1 g per kg of body weight per day.

* * * * *